United States Patent [19]

Knapp, Jr.

[11] 4,215,045
[45] Jul. 29, 1980

[54] $^{123m}$TE-LABELED BIOCHEMICALS AND METHOD OF PREPARATION

[75] Inventor: Furn F. Knapp, Jr., Oak Ridge, Tenn.

[73] Assignee: The United States of America as represented by the United States Department of Energy, Washington, D.C.

[21] Appl. No.: 920,411

[22] Filed: Jun. 29, 1978

[51] Int. Cl.² ............................................. C07J 9/00
[52] U.S. Cl. ..................................... 260/397.2; 424/1
[58] Field of Search ...................... /Steroids MS File; 260/397.2

[56] References Cited

U.S. PATENT DOCUMENTS 4,041,145   8/1977   van der Veek ................... 260/397.2

OTHER PUBLICATIONS

Basmadjian et al., Jour. of Nuclear Medicine, vol. 19, No. 6, pp. 689, 718.
Knapp; F. F. et al., "Journal of Nucl. Med.", vol. 18, No. 6, pp. 600 and 610, Jun. 1977.

*Primary Examiner*—Elbert L. Roberts
*Attorney, Agent, or Firm*—R. V. Lupo; Stephen D. Hamel

[57] ABSTRACT

A novel class of $^{123m}$Te-labeled steroids and amino acids is provided by the method of reacting a $^{123m}$Te symmetric diorgano ditelluride with a hydride reducing agent and a source of alkali metal ions to form an alkali metal organo telluride. The alkali metal organo telluride is reacted with a primary halogenated steroidal side chain, amino acid, or amino acid precursor such as hydantoin. The novel compounds are useful as biological tracers and as organal imaging agents.

31 Claims, No Drawings

$^{123m}$TE-LABELED BIOCHEMICALS AND METHOD OF PREPARATION

BACKGROUND OF THE INVENTION

This invention was made in the course of, or under, a contract with the United States Department of Energy. It relates to the preparation of $^{123m}$Te-labeled organic compounds useful as tracers for the study of metabolic pathways and physiological research. Additionally, certain of the compounds of this invention have utility as radioactive imaging agents for the detection of systemic or organal disorders.

The use of radioactively labeled organic compounds in the study of biochemical reactions is well known. Tritium, $^{14}$C and $^{32}$P have been used extensively since their corresponding stable isotopes are present in practically all important cellular components. Biochemical agents labeled with radionuclides such as $^{99m}$Tc and $^{75}$Se have found application as scintigraphic imaging agents for the detection of abnormally functioning tissues and pathophysiological conditions such as cancer. A number of adrenal disorders are characterized by an increased or decreased uptake of steroids. For example, aldosteroma is characterized by a hyperactive uptake of steroids from the blood. A patient's uptake of radioisotopically labeled steroids will indicate which adrenal gland is involved. Any radioactive steroid which accumulates in the adrenals is useful as an imaging agent for the detection of hyper- annd hypoactive disorders. A diagnosis can be made by a comparison of adrenal uptake and metabolism of labeled compounds with that of normal adrenals.

Steroids labeled with $^{131}$I and $^{75}$Se have been proposed as adrenal imaging agents. Results in laboratory animals and humans have shown acceptable adrenal accumulation of the agents. Good quality images of human adrenals can be obtained. The use of $^{75}$Se-labeled 3-beta-hydroxy-19-(methyl seleno)-cholest-5-ene is described in S. D. Sarkar et al in Journal of Nuclear Medicine, Vol. 16, p.1038 (1975).

One disadvantage associated with $^{131}$I labeled adrenal agents is that the radioiodinated steroids were very unstable in vivo resulting in high thyroid accumulations of radioactive iodine. Additionally, $^{131}$I labeled agents have a limited shelf life and their use results in a high beta absorbed dose. The $^{75}$Se nuclide decays with the emission of two high energy photons which result in inefficient collimation and poor quality images.

Certain of the prior art difficulties could be avoided by the use of $^{123m}$Te-labeled agents as suggested in by the use of $^{123m}$Te-labeled agents as suggested in *Radioactive Pharmaceuticals*, Andrews et al. CONG-651111, Springfield, Virginia, National Bureau of Standards 1966 p.118. German Pat. No. 2,553,408 also suggests the use of $^{123m}$Te-labeled compounds and describes the synthesis of a steroid having nonradioactive tellurium present at position 19.

All $^{123m}$Te-labeled steroids of this invention are useful as tracers in physiological studies. Another utility of $^{123m}$Te-labeled steroids is for the preparation of $^{123m}$Te-labeled liposomes. Since liposomes have been suggested as carriers for a variety of drugs and chemotherapeutic agents, the $^{123m}$Te-labeled liposomes can provide a non-invasive technique for the study of their fate in vivo. To prepare $^{123m}$Te-labeled liposomes, the labeled steroids of this invention are substituted for steroids in the conventional liposome preparation techniques, such as described in D. Papahadjopoulos et al. Biochim. Biophys. ACTA. Vol. 135 p.624–638 (1967) and A. D. Bangham et al., Journal of Mol. Biol. Vol. 13, p. 238–252 (1965), both of which are incorporated herein by reference. The labeled liposomes are administered in the normal manner and their transport through the body is monitored by conventional radiographic techniques. Another use of labeled steroids is in the study of lipoprotein metabolism. Lipoproteins are formed in the liver when steroids are injected into the body. Lipoproteins formed from $^{123m}$Te-labeled steroids can be recovered from the blood by conventional techniques. The labeled lipoproteins can be reinjected and their metabolism studied by radiographic techniques.

Another useful class of tracer compounds are radioactively labeled amino acids. Labeled amino acids have been used in the study of protein metabolism and synthesis, for example, that taking place in the pancreas. Labeled amino acids are also useful in the study of the effects of various pharmaceuticals on protein metabolism.

$^{123m}$Te-labled amino acids are likely to be isoteric with the sulfur analogs and behave similarly in vivo. Additionally, the high quality scintigraphic images produced by the $^{123m}$Te nuclide is a substantial improvement over prior art labeled amino acids. Prior art attempts to prepare telluro-amino acids by microbiological methods have been unsuccessful, see Kolar Z., Int. J. Appl. Radiat. Isot. 25 330 (1974).

SUMMARY OF THE INVENTION

It is an object of this invention to provide $^{123m}$Te-labeled biochemicals.

It is a further object to provide a process of synthesis for $^{123m}$Te-labeled biochemicals.

These and other objects are achieved in a process for the preparation of $^{123m}$Te-labeled organic compounds of the formula R-$^{123m}$Te-CH$_2$-R′, R being alkyl, substituted alkyl, aryl, or substituted aryl and R′ being a steroidal side chain, amino acid group or alkyl amino acid group said process comprising the steps of:

(a) reacting a $^{123m}$Te-symmetric diorgano ditelluride, R$_2$$^{123m}$Te$_2$, R being an alkyl, aryl, substituted alkyl or substituted aryl, with a hydride reducing agent and a source of alkali metal ions to form an alkali metal organo telluride M-$^{123m}$Te-R;

(b) reacting said alkali metal organo telluride with a primary halogenated organic compound R$_a$′—X, R$_a$′ being a steroidal side chain group, an alkyl amino acid group, or a group hydrolyzable to an alkyl amino acid group.

A convenient method of preparing the amino acids is for R$_a$′ to be a 5-hydantoin or 5-alkyl hydantoin, which is hydrolyzed under basic conditions after reaction with the alkali metal organo telluride.

Symmetric diorgano ditellurides can be prepared by reacting a dialkali metal ditelluride M$_2$$^{123m}$Te$_2$ with a halogenated organic compound R—X. Alternatively, the diorgano ditelluride can be formed by reacting $^{123m}$Te with an organo magnesium halide, R—Mg—X. This method is preferable when R is an aryl group.

The most preferable hydride reducing agent is NaBH$_4$, which both reduces the diorgano ditelluride and provides a source of Na ions to form Na-$^{123m}$Te-R.

DETAILED DESCRIPTION

One aspect of this invention involves a synthesis of $^{123m}$Te-labeled steroids by methods which introduce the Te into the side chain rather than the steroid nucleus. The general formula for the labeled steroids of this invention is R-$^{123m}$Te-R' where R can be alkyl, substituted alkyl, aryl and substituted aryl and R' is a steroidal side chain group. As used herein, the steroidal side chain group is defined as an alkyl group attached to the No. 17 carbon atom of the well known cyclopentanophenanthrene nucleus as shown below.

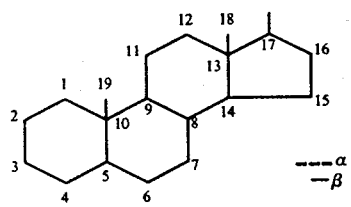

Without departing from the spirit of this invention, the steroid nucleus can contain 1 or more double bonds, such as between the 5 and 6 carbons. The steroid can be substituted with a number of substituents in a variety of positions, for example the 3 beta position can be substituted with hydroxy, methoxy, or esters of fatty acids, such as palmitic, steric, or oleic acid. The side chain attached to the number 17 carbon atom can be lower alkyl (1-4 carbon atoms) or higher alkyl (5 or more carbon atoms) and can also contain various functional groups. The introduction of tellurium into 5-alpha steroids rather than 5-beta steroids preserves the trans geometry of the steroid nucleus, which is generally desirable for biological activity such as adrenal concentration. Due to apparent steric effects, the side chain carbon atom adjacent the Te must be a primary carbon atom. Te was introduced into the side chain because of the many degrees of freedom of this region of the molecule. The Te heteroatom could thus be more readily accomodated in the side chain. The steroids labeled in the side chain appear to demonstrate greater relative adrenal uptake than prior art steroids labeled at the 19 or 6 positions. Due to the general instability of telluro organic compounds, the present synthesis method minimizes the need for isolating intermediates. All that is necessary to provide the side chain $^{125m}$Te-labeled steroids of this invention is that a steroid with a primary halogenated side chain carbon atom, $R_a'$—X be reacted with a $^{123m}$Te-alkali metal organo telluride. The alkali metal organo telluride is prepared by reacting a $^{123m}$Te-symmetric diorgano ditelluride with a hydride reducing agent and a source of alkali metal ions. The following general steps lead to the preparation of side chain $^{123m}$Te-labeled steroids. It will be apparent to those skilled in the art that the steps are applicable to the preparation of a variety of compositions.

A. General Procedures for Preparation of $^{123m}$Te $^{123m}$Te is conveniently prepared from isotopically-enriched $^{122}$Te, obtainable from the isotope sales office of the Oak Ridge National Laboratory, Oak Ridge, Tennessee, 37830. The irradiation of this isotope in a neutron flux provides a $^{123m}$Te isotope. Generally, irradiation will result in melting of target metal resulting in a hard mass upon cooling. The target is taken into solution in an acid solution such as aqua regia, which is evaporated to dryness to provide a tellurium salt. The salt can be redissolved in acid such as HCl and again evaporated to dryness to assure complete removal of nitrates. The resulting solid is dissolved in water. A reducing agent, NaBr, is added to reduce Te(VI) to Te(IV) and the solution is boiled for one-half hour to accelerate the reaction. SO$_2$ is bubbled through the solution to reduce Te(IV) to Te(O) causing the precipitation of tellurium metal which can be recovered by filtration, etc. This procedure is a modification of the method of H. P. Hupf et al., Internat. J. Appl. Radiat. and Isotopes, 19, 345–351 (1968). $^{123m}$Te can be combined with carrier (non-radioactive) Te in the initial Te dissolution steps to reduce the specific activity to the desired level. Since the chemistry of the process is independent of the isotopic properties of Te, portions of the method are illustrated with reference to Te with the understanding that some or all of the Te can be in the $^{123m}$Te form to prepare the compositions of this invention.

B. Preparation of An Alkali Metal Alkyl Telluride

The preparation of a dialkali metal ditelluride is achieved by the direct reaction of tellurium powder with an alkali metal. This is conveniently achieved by reaction in liquid ammonia to form M$_2$Te$_2$, M being any alkali metal. M$_2$Te$_2$ is then converted to the desired dialkyl-ditelluride R$_2$Te$_2$. Since M$_2$Te$_2$ is unstable, it is reacted in situ by the direct addition of the appropriate alkyl halide R-X to form a dialkyl-ditelluride. It is essential that R—X be added only after the M$_2$Te$_2$ is formed to prevent alkylation of intermediate M$_2$Te to form R$_2$Te. The reaction product is extracted with a suitable organic solvent such as benzene, diethyl ether, ethyl acetate, methanol, ethanol, hexane etc. with benzene preferred. The extracted dialkyl ditelluride is reduced and contacted with a source of alkali metal ions to form an alkyl alkali metal telluride M—Te—R. The reducing agent is preferably an alkali metal borohydride such as NaBH$_4$ which reduces the ditelluride and forms the alkali metal alkyl telluride. To ensure complete conversion to R—Te—M, MOH can be added to the mixture and refluxed. Alternately, reduction can be performed by Na metal in liquid NH$_3$, sodium formaldehyde sulfoxylate, and other reducing agents. The reduced product is an alkali metal alkyl telluride.

According to the general method of this invention, the alkali metal alkyl telluride M—Te—R is reacted with any halogenated organic compound R'—CH$_2$—X to form R—Te—CH$_2$—R'.

C. Preparation of Steroidal Halides

If the appropriate steroid with a halogenated primary carbon is not available, it can be prepared from bile acids and other steroids containing side chain carboxylic groups by a modified Hunsdiecker degradation. This degradation comprises reaction of an appropriate steroid with mercuric oxide and bromine, Hg$_2$O—Br$_2$ in refluxing carbon tetrachloride, and is described in detail in Cristol, S. J. et al., J. Org. Chem. 26, 280 (1971) herein incorporated by reference. The result of the modified Hunsdiecker degradation is a steroidal norhalide. Other steroids with halogenated side chains can be prepared by direct reduction of bile acids to the corresponding alcohol, followed by halogenation with CBr$_4$ in triphenyl phosphene to provide a steroidal halide. This procedure is suitable for steroids that contain double bonds and therefore cannot be directly halogenated.

D. Preparation of Alkyl Telluro Steroids

The steroidal-halide or nor-halide is reacted directly with the alkali metal alkyl telluride product of step B. This can be performed by direct addition of the halide as a slurry in a suitable organic solvent, for example benzene. The resulting telluro steroid can be recovered by absorption chromatography.

E. Preparation of $^{123m}$Te-labeled Amino Acids

The preparation of telluro amino acids also involves the reaction of a halogenated organic compound with an alkali metal telluride. Unlike the seleno compounds used in the prior art, some alkyl telluro compounds are too unstable for use even at the site of formation. Attempts to introduce tellurium from benzyl tellurides into amino acids have been unsuccessful due to decomposition of benzyl tellurides. It has been found that the instability of benzyl tellurides can be overcome by the use of aryl tellurides. The general procedure for labeling amino acids with aryl tellurides is as follows.

1. Preparation of $^{123m}$Te-labeled Diaryl Ditellurides

Aryl halides do not react with $Na_2Te_2$ in liquid ammonia as do alkyl halides. Aryl magnesium chloride can be directly reacted with a solution or slurry of Te. In some cases the reaction can be initiated by the addition of a small amount of benzoyl peroxide.

2. Preparation of Phenyl Telluride

The diaryl ditelluride from step A is reacted with a reducing agent such as an alkali metal borohydride to provide an alkali metal aryl telluride R-Te-M.

3. Preparation of Telluro Amino Acid

This is readily accomplished by reaction with a halogenated compound which can be hydrolyzed to form an amino acid, for example a halogenated hydantoin as shown.

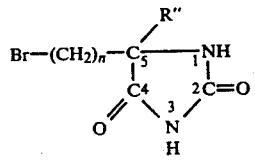

R" is hydrogen, alkyl, substituted alkyl, aryl, or substituted aryl. This method is similar to prior art methods of preparing seleno amino acids, See Klosterman, H. J. et al., J. Am. Chem. Soc. 69 2009 (1947). A halogenated hydantoin such as the above 5(haloalkyl)hydantoin is reacted with an alkyl or aryl tellurol to form an alkali metal salt of 5(alkyl or aryl telluro) alkyl hydantoin. For increased yield, alkyl telluro alkyl hydantoin salts should be acidified with $H_2SO_4$. Aryl telluro alkyl hydantoin salts can be acidified with HCl. Hydrolysis in basic solutions provides the corresponding alpha amino acid.

The following examples illustrate the preparation of several representative $^{123m}$Te-labeled compounds.

EXAMPLE I

Preparation of $^{123m}$Te

Isotopically enriched $^{122}$Te (94.71%), about 50 mg, obtained from the isotope sales office of the Oak Ridge National Laboratory, was irradiated for 14 days in the Oak Ridge High Flux Isotope Reactor at $2 \times 10^{15}$ neutrons/cm$^2$.sec. The reactor irradiation of the metallic tellurium resulted in the formation of a molten target mass which had solidified during cooling. The target was dissolved in aqua regia and the solution taken to insipient dryness. The solid residue was dissolved in concentrated hydrochloric acid and taken to incipient dryness again. The acid treatment was repeated again and the resulting solid was dissolved in 200 ml of water. After the addition of NaBr (5 grams) the solution was boiled for one-half hour, cooled, and $SO_2$ was passed through the solution at the rate of two bubbles per second for two hours. The tellurium metal precipitated as very fine particles and was recovered by centrifugation. The recovered particles were washed three times with water and dried in an oven at 140° C. The recovery of $^{123m}$Te is consistently better than 90% by this method.

EXAMPLE II

Preparation of Disodium Ditelluride 22 milligrams, 25.8 mCi of $^{123m}$Te was combined with carrier tellurium, (45 micron powder) to yield a sample with a specific activity of 25.8 mCi/mmole. Approximately 25 ml liquid ammonia was condensed into the reaction vessel containing the tellurium powder. The ammonia is maintained in the liquid state by inserting the flask in a bath of acetone and dry ice (−40°--−70° C.). The reaction vessel had been previously flushed with argon and connected to a small trap to maintain a slight argon pressure during the reaction. Freshly cut pieces of metallic sodium (23 mg, 1 mole) were added to the rapidly stirred slurry. The solution was stirred 2 hours and progressed through the color changes yellow, green, blue, red. The red color indicated the completion of $Na_2Te_2$ formation.

EXAMPLE III

Preparation of Dialkyl Ditelluride

Isopropyl iodide (174 mg, 1 mmole) was added to the reaction vessel of Example II by means of a syringe inserted through a rubber septum. The initial deep red color of the solution slowly turns to yellow amber concomitant with the appearance of colloidal tellurium. After one hour of stirring the ammonia was allowed to evaporate under a stream of argon yielding a residue consisting of an orange gum containing metallic tellurium. The residue was extracted with several small portions of benzene (15 ml.) and the combined extracts were washed with water several times. The benzene solution was diluted with methanol to 25 ml. and aliquots were taken for counting. The benzene extracted material indicated a 42% yield of $^{123m}$Te di-isopropyl ditelluride.

EXAMPLE IV

Preparation of sodium alkyl telluride

The $^{123m}$Te diisopropyl ditelluride solution from Example III was combined with 25 ml. of methanol (2:1 benzene/methanol ratio). The mixture was stirred vigorously under an argon atmosphere. Small portions of sodium borohydride were then added until a colorless solution was obtained which indicated complete reduction of the ditelluride to the sodium isopropyl telluride. In some cases gentle warming of the ditelluride solution is needed to initiate the reduction.

EXAMPLE V

Preparation of a steroidal-nor-bromide

The following is a modified Hunsdeicker synthesis for the preparation of steroidal nor-bromides from a bile acid. A bile acid, 3-alpha-acetoxy-5-beta-cholan-4-oic acid (1.65 g, 3.95 mmoles) and red mercuric oxide (1.1 g, 5.10 mmoles) were stirred vigorously while refluxing in the dark in 50 ml of $CCl_4$. To this mixture, 2.2 ml of a bromine solution in $CCl_4$ (500 mg/ml, 6.9 mmoles) was added dropwise over a 5 min. period. The progress of the reaction was monitored by thin layer chromotography. After 1.5 hr. the reaction was complete. The mixture was filtered while hot and the pink precipitate washed thoroughly with warm benzene. The combined filtrates were concentrated in vacuo to yield a dark gummy solid, which was dissolved in warm benzene and applied to a fully active neutral alumina column (5×15 cm.) that had been slurried in the same solvent. The column was eluted with increasing volumes of ethyl ether in benzene. The product was eluted with 25 vol.%–75 vol.% ether-benzene fractions and the solvent was removed in vacuo to yield a white solid. Crystallization from ether/methanol gave 53% yield of 3-alpha-acetoxy-24-nor-23-bromo-5-alpha-cholane; max infrared frequency (KBr) 1720 cm$^{-1}$ (C=O); mass spec. ions at m/e 454 and 452 (M; 2% and approx. 1.5%), 394 and 392 (M—CH$_3$COOH; 49% and 48%), 379 and 377 (M—CH$_3$—CH$_3$COOH; 13% and 13%), 352 and 350 (3% and 3%), 340 (7%), 339 (5%), 338 (5%), 327 and 325 (1% and 1%), 313 (4%), 229 (2%), 228 (2%), 227 (3%), 290 (3%), 284 (4%), 275 (3%), 271 and 269 (1% and 1%), 257 (8%), 243 and 241 (1% and 1%), 230 (48%), 217 (29%), 216 (48%), 215 (100%), and 201 (13%); n.m.r. 0.66 (s, 3H, C-18-CH$_3$), 0.91 (d, J=6 Hz, 3H, C-21-CH$_3$), 0.96 (s, 3H, C-19-CH$_3$), 2.02 (s, 6H, acetate CH$_3$'s), 3.38 (m, 2H, C-23-H's) and 4.70 (m, 1H, C-3alpha-H).

EXAMPLE VI

Preparation of 3-beta-hydroxy-24-nor-23(isopropyltelluro)-5-alpha-cholane

To a sodium isopropyl telluride solution prepared as in Example IV is added about 80 mg. (2 mmole) of sodium hydroxide and the mixture is refluxed to ensure formation of the Na—Te—R telluride. 112 milligrams of 3-beta-acetoxy-24-nor-23-bromo-5-alpha-cholane prepared from 3-beta-acetoxy-5-alpha-cholan-24-oic acid by the same general procedure of Example V is added to the colorless solution as a slurry in a small volume of benzene and the mixture was refluxed for 1 hour. The NaOH hydrolyzed the 3 beta acetoxy group to hydroxy. After this time period the reaction is completed. The resulting solution is poured into water and the organic layer washed several times with water. The yellow-colored benzene solution is applied to a silicic acid column, slurried in benzene. 25 ml fractions are collected by elution with increasing concentrations of ethyl ether in benzene. The product is eluted at about 2 vol.% ether:98 vol.% benzene and has the following structural formula

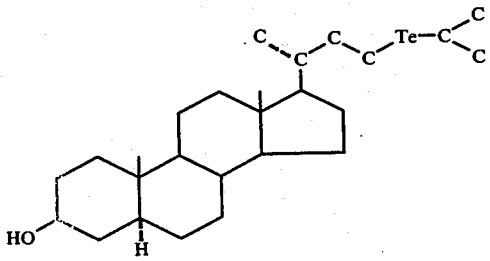

EXAMPLE VII

Preparation of 3-alpha-hydroxy-24-nor-23-(isopentyltelluro)-5-beta-cholane 3-alpha-acetoxy-24-nor-23-bromo-5-beta-cholane, prepared by a modified Hunsdiecker synthesis from lithocholic acid acetate by the general procedure described in Example V, is added to a methanolic solution of sodium isopentyl tellurol prepared as in Example IV from diisopentyl ditellurides prepared by the procedure in Example III using isopentyl iodide. The solution was refluxed for one hour after which time thin layer chromotography indicated the reaction to be complete. The solution was poured into water and extracted with chloroform. The yield was (32%). The material can be purified by a thin layer chromatography using a silica gel H absorbent and chloroform solvent; mix infrared frequency (KBr) 3330 cm$^{-1}$ (—OH); mass spec., 532 (M, 14%), 514 (M—H$_2$O, 14%), 461 (M—C$_5$H$_{11}$, 15%), 443 (M—H$_2$O—C$_5$H$_{11}$, 7%), 415 (1%), 394 (3%), 392 (3%), 353 (2%), 331 (5%), 328 (6%), 313 (12%), 302 (7%), 299 (7%), 297 (10%), 285 (8%), 278 (12%), 273 (9%), 257 (M-side chain, 44%), 243 (9%), 229 (15%), 215 (52%), and 201 (25%); high resolution mass spec., 532.2884 (calculated for C$_{28}$H$_{50}$OTe:532.2898); n.m.r., 0.62 (s, 3H, C-18-CH$_3$), 0.92 (s, 3H, C-19-CH$_3$), 0.93 (d, J=6 Hz, 3H, C-21-CH$_3$), 2.60 (complex multiplet, 4H, methylene hydrogens flanking the tellurium) and 3.58 (m, 1H, c-3 alpha-H).

EXAMPLE VIII

Preparation of 3-alpha-hydroxy-24-nor-23-(isopropyl telluro)-5-beta-cholane

A solution of sodium isopropyl telluride was prepared by reduction of diisopropyl ditelluride (135 mg, 400 micro moles) with sodium borohydride in basic methanol in the manner of Examples I–IV. 3-alpha-acetoxy-24-nor-23-bromo-5-beta-cholane (90 mg, 200 micro moles) was added and the mixture was refluxed two hours. Purification was performed by thin layer chromatography using chloroform solvent, giving 3-alpha-hydroxy-24-nor-23-(isopropyl telluro)-5 beta-cholane as a gummy semisolid that could not be adequately crystallized from a variety of solvents; max infrared freq. (KBr) 3360 cm$^{-1}$(—OH); mass spec., 504 (M, 8%), 486 (M—H$_2$O, 12%), 461 (M-isopropyl, 2%), 443 (M-H$_2$O-isopropyl, 8%), 349 (1%), 332 (3%), 330 (4%), 313 (16%), 299 (9%), 297 (14%), 285 (8%), 283 (6%), 278 (8%), 273 (23%), 271 (8%), 260, (9%), 257 (43%), 255 (55%), 243 (7%), 241 (8%) 233 (6%), 231 (10%), 230 (15%), 229 (13%), 219 (5%), 217 (12%), 215 (58%), 211 (6%), 203 (22%), and 201 (28%); high resolution mass spec. 504.2564 (calculated for C$_{26}$H$_{46}$OTe:504.2584); n.m.r., 0.63 (s, 3H, C-18-CH$_3$), 0.92 (s, 3H, C-19-CH$_3$), 0.93 (d, J=6 Hz, 3H, C-21-CH$_3$), 1.60 (d, J=6 Hz, 6H, C-26, and C-27-CH$_3$'s), 2.64 (m, 2H, C-23-H's), 3.38 (m, 1H, C-25-H), and 3.57 (m, 1H, C-3 alpha-H).

EXAMPLE IX

Preparation of 3-Beta-hydroxy-24-nor-23-(isopentyl telluro)-5-alpha-cholane 3-beta-acetoxy-24-nor-23-bromo-5-alpha-cholane was prepared by the modified Hunsdiecker degradation of 3-beta-acetoxy-5-alpha-cholanic acid and purified, exactly as described in Example V. The product was crystallized from methanol and water to give fine needles. To this material in refluxing methanol was added 200 mmoles of sodium isopentyl tellurol. The reaction mixture was poured into water and the crude product extracted with chloroform. Purification by thin layer chromatography gave a thick gum. The product was homogeneous by thin layer chromatography analysis and trituration with a small volume of ether gave a solid having a melting point of 78° to 80° C.; max infrared freq. (KBr) 3300 cm$^{-1}$(—OH); mass spec., 532 (M, 48%), 514 (M—H$_2$O, 57%), 461 (M—C$_5$H$_{11}$, 10%), 443 (M—H$_2$O—C$_5$H$_{11}$, 17%) 415 (2%), 349 (2%), 331 (3%), 313 (21%), 303 (2%), 299 (3%), 297 (7%), 285 (12%), 273 (15%), 257 (M-side chain, 30%), 225 (19%), 243 (8%), 229 (39%), 215 (28%) and 201 (20%). High resolution mass spec.; 532.2843 (calculated for C$_{28}$H$_{50}$OTe 532.2883).

The 3-hydroxy-24-nor-23-(alkyl telluro) steroids are relatively insoluble in ether but are readily extracted from reaction mixtures with chloroform or ethyl acetate. The 5 alpha steroids were designed for adrenal imaging, however the synthesis steps were developed using 5 beta steroids which were less expensive. No difference was noted in the synthetic procedures of the cis or trans steroids.

EXAMPLE X

Example X describes the preparation of 3-beta-hydroxy-24 (isopropyl telluro) chol-5-ene, containing a double bond between carbons 5 and 6 in the steroidal nucleus, and having the structural formula

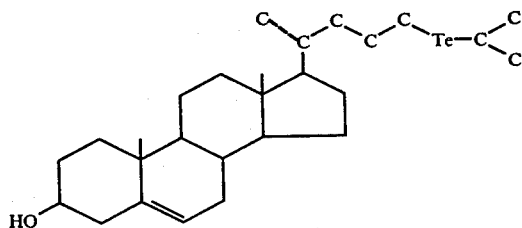

Methyl-3-beta-hydroxy-chol-5-en-24-oate (3 g), was dissolved at room temperature in 10 ml of trimethylorthoformate with stirring. A 72% perchloric acid solution (600 microliters) was added dropwise over a 10-min period. The mixture was stirred 2 h and allowed to stand overnight. Ethyl ether was added to the resulting brown sludge with stirring. Most of the solid dissolved and the ether solution was washed successively with water and a saturated NaHCO$_3$ solution. Following a final water wash the solution was dried over anhydrous Na$_2$SO$_4$ and evaporated in vacuo to yield a white solid. Crystallization from MeOH—H$_2$O gave 2.99 g of methyl-3-beta-methoxy-chol-5-en-24-oate as needles of the methyl ether, mp 108°-109° C. This methyl ether was dissolved in 50 ml of tetrahydrofuran and the reaction system flushed with argon. A 70% solution of Vitride [sodium bis-(2-methoxy ethoxy)aluminum hydride] in C$_6$H$_6$ (3 ml), was added dropwise and the solution refluxed 1 hour. The reaction was cooled and water added cautiously until the vigorous hydrolysis reaction ceased. The mixture was poured into water and the crude product extracted with ethyl ether. The combined organic extracts were washed with water, dried over anhydrous Na$_2$SO$_4$ and evaporated in vacuo to yield 3-beta-methoxy-24-hydroxy-chol-5-ene as a white solid. Crystallization from Me$_2$CO in the refrigerator gave 1.59 g of fine needles of the alcohol; m.p. 154°-154.5° C. This alcohol (450 mg) was dissolved in dry Et$_2$O (50 ml) to which was added CBr$_4$ (700 mg). A solution of triphenylphosphine (550 mg) in Et$_2$O (10 ml) was added dropwise to this mixture. The system was flushed with argon and the solution stirred for 8 h at room temperature. Analysis by thin layer chromatography (C$_6$H$_6$) indicated the presence of a substantial amount of starting material (R$_f$ 0.02) and an approximately equal amount of the suspected product 3-beta-methoxy-24-bromo-chol-5-ene(R$_f$ 0.40). Additional CBr$_4$ (700 mg) and triphenylphosphine (550 mg) were added and the solution stirred overnight. Analysis by TLC then indicated the reaction to be complete. The ether solution was washed several times with H$_2$O, dried over anhydrous Na$_2$SO$_4$ and the solvent removed in vacuo to give a gummy solid. Crystallization from Me$_2$CO—H$_2$O gave 398 mg of 3-beta-methoxy-24-bromo-chol-5-ene (R$_f$ 0.40) as micro-crystals: mp 122.5°-123.5°. The 3 beta-methoxy-24-bromo-chol-5-ene (97 mg) was dissolved in 3 ml of a 2:1 mixture of EtOAc—Ac$_2$O. Anhydrous FeCl$_3$ (5 mg, 0.033 micromoles) was added and the brown-colored solution stirred 72 h at room temperature under a drying tube. The crude reaction mixture was taken to dryness in vacuo and the resulting dark gum dissolved in C$_6$H$_6$. This solution was applied to a 2-cm diameter silicic acid column (25 g, 60–200 mesh) and fractions 100 ml in volume were eluted. Hexane eluted a non-polar component which was identified as 3 beta-chloro-24-bromo-chol-5-ene. Crystallization from MeOH—H$_2$O gave 14.2 mg of plates: mp 137°-138° C. The 3 beta-acetoxy-24-bromo-chol-5-ene (90 mg) was added to a refluxing solution of sodium isopropyl telluride (0.40 mmol) prepared in the manner of Example IV. After 30 min TLC analysis demonstrated the presence of a major U.V. absorbing product (CHCl$_3$, R$_f$ 0.23). The reaction mixture was poured into water and the crude product extracted with CHCl$_3$. Following evaporation of the solvent in vacuo the resulting yellow gum was dissolved in C$_6$H$_6$ and this solution applied to a 2-cm diameter silicic acid (25 g, 60–200 mesh). The column was washed with C$_6$H$_6$ and the desired product eluted with 10% Et$_2$O—C$_6$H$_6$. Evaporation of the solvent gave 62.2 mg of 3-beta-hydroxy-24-(isopropyl telluro-chol-5-ene. IR (KBr) 3360 cm$^{-1}$ (OH), 1195, 1145, 1055, 965, 840 and 800 cm$^{-1}$; NMR 0.66 (s, 3H, C-18), 0.94 (d, J=6 Hz, C-21), 1.00 (s, 3H, C-19), 1.69 (d, J=7-8 Hz, 6H, terminal isopropyl Me's), 2.61 (d of d, J=7-8 Hz, 2H, C-24), 3.40 (n, J=6 Hz, C-25), approx. 3.46 (m, 1H, C-3), 5.30 (m, 1H, C-6H); mass spec. 516 (M, 62), 498 (M—H$_2$O, 3), 455 (M—H$_2$O—C$_3$H$_7$), 441 (M—H$_2$O—CH$_3$—C$_3$H$_6$, 2), 389 (M-127, 2), 361 (M-154, 3), 343 (3), 325 (17), 283 (5), 271 (6), 10 255 (M—H$_2$O-side chain, 21), 241 (5), 205 (13), 203 (17).

Due to the presence of the double bond in the bile acid precursor, the Hunsdiecker synthesis is unsuitable to produce a steroidal primary bromide.

Examples XI-XIV illustrate the preparation of telluro amino acids by reaction of alkyl or aryl alkali metal tellurides with 5-halo alkyl hydantoins. If primary halogenated amino acids are available, they may be reacted directly with the telluride.

EXAMPLE XI

5(beta-bromo ethyl)hydantoin

DL-homoserine (36 g.) was dissolved in $H_2O$ (100 ml) and the solution heated to 60° C. in an oil bath. A mixture of KCNO (26 g.) in $H_2O$ (50 ml) was added dropwise to the amino acid solution over a 5 min. period. The resulting solution was stirred over a 3-hour period at 60°–65° C. The temperature was elevated to 90° C. after the cautious dropwise addition of a 48% HBr aqueous solution (100 ml). The temperature was maintained at 90°–95° C. and the solution then cooled to room temperature and allowed to stand overnight. After evaporation in vacuo, 300 ml of acetone were added to the resulting red gum. The solution was stirred vigorously and a white crystalline precipitate was removed by filtration. The filter cake was washed thoroughly with acetone and the combined acetone filtrates taken to dryness in vacuo. The resulting red gum was dissolved in $H_2O$ (100 ml) and placed under refrigeration. The tan colored precipitate was obtained by filtration and dissolved in acetone. Hexane was added to the rapidly stirred acetone solution resulting in the deposition of a fine white solid, identified as 5(beta-bromo ethyl)hydantoin.

EXAMPLE XII

DL-alpha-Amino-gamma-(Phenyl Telluro)Butyric Acid

Reactor produced $^{123m}Te$ (65.5 mg, 26.3 mCi) was combined with 188.5 mg of carrier Te powder. This material was stirred in tetrahydrofuran (5 ml) to which was added phenyl magnesium chloride (4 mmole) in the same solvent (2 ml). The mixture was stirred rapidly and refluxed but the reaction did not commence as indicated by the absence of the orange-colored product. After the addition of a small crystal of benzoyl peroxide, reaction began immediately. The orange-colored solution was refluxed 1 minute and the reaction flask flushed with $O_2$ and cooled in an ice bath. After warming to room temperature, the solution was stirred 30 minutes, filtered, and the orange-colored filtrate diluted with benzene to a final volume of 25 ml. Aliquots of this solution were counted. The $^{123m}Te$-labeled diphenyl ditelluride contained 9.22 mCi of radioactivity. The benzene solution was diluted to 50 ml with methanol and the $^{123m}Te$-labeled diphenyl ditelluride reduced with $NaBH_4$ in the manner described in Example IV. To this mixture was added 208 mg, 1 mmole of 5-(beta-bromo ethyl)hydantoin prepared as in Example XI. The mixture was poured into water and extracted with benzene to remove diphenyl ditelluride and other non-polar material. The aqueous layer was acidified to pH 1-2 with 6 N HCl and extracted thoroughly with ether. The combined organic extracts were washed well with water, dried over anhydrous sodium sulfate and the solvent removed in vacuo to give 2.2 mCi of $^{123m}Te$-labeled 5-(beta[phenyl telluro]ethyl)hydantoin. This hydantoin is dissolved in 1 N NaOH (2 ml) and heated in a polytetrafluoroethylene-lined bomb by heating at about 165°–167° C. for one hour. Upon cooling, the solution is extracted with benzene and 1 N HCl is added to adjust the pH to 7-8, to provide $^{123m}Te$-labeled DL-alpha-amino-gamma-(phenyl telluro)butyric acid.

EXAMPLE XIII

DL-alpha-amino-gamma-(methyl telluro)butyric acid

Sodium ditelluride ($Na_2Te_2$) is generated by reaction of Te powder (45 micron) with metallic sodium in liquid ammonia as described in Example II and alkylated with methyl iodide as described in Example III to provide dimethyl ditelluride (approx. 11 mmole) addition of $NaBH_4$ in benzene/methanol (1:1) under an argon atmosphere generates sodium methyl telluride. 5-(beta-bromo ethyl)hydantoin prepared as in Example XI (880 mg 4.2 mmole) is added in a small volume of methanol and the mixture stirred at room temperature for 30 min. The mixture is poured into water and the aqueous solution extracted with benzene, acidified to pH 2-3 with 10% $H_2SO_4$ and extracted with ethyl acetate. The desired product is in the ethyl acetate layer which is washed with water, dried over anhydrous $Na_2SO_4$ and evaporated to dryness in vacuo. The resulting tan-colored solid was crystallized from acetone-petroleum ether to give a white solid. The white solid (40 mg, 0.15 mmole) is hydrolyzed with a 2 molar excess of 1 N NaOH in a polytetrafluoroethylene-lined bomb at about 165° C. for about one hour. The solution is carefully acidified to pH 5–6 with 10% $H_2SO_4$, filtered and lyophilized to give a tan solid, which was identified by mass spectroscopy, n.m.r., I.R., and U.V. spectroscopy, as DL-alpha-amino-gamma-(methyl telluro)butyric acid.

EXAMPLE XIV

DL-alpha Amino-alpha Methyl-beta(Phenyl Telluro) and DL-alpha Amino-alpha Ethyl-beta(Phenyl Telluro) Propionic Acids The preparation of 5-bromo-methyl, 5-methyl hydantoin and 5-bromomethyl, 5-ethyl hydantoin are described by S. Tahara et al. in Agricultural Biol. Chem. Vol. 35, (1971) pp. 53–57 and pp. 1806–1809 which are herein incorporated by reference. Each of the hydantoins is reacted with sodium phenyl telluride as described in Example XIII and hydrolyzed to provide the telluro amino acids; $R-^{123m}Te-CH_2-R'$, where $R'$ is $CH_2CR''(NH_2)COOH$, where $R''$ is methyl or ethyl.

Tissue Distribution Studies

Fisher strain white albino rats were used for the following investigation. The animals were six to ten weeks old, male rats weighed 225–300 grams and the female rats weighed 160–180 grams. Food and water were allowed ad libitum prior to injection throughout the duration of the experiment. Benzene solution of the $^{123m}Te$-labeled steroid of Example VI was taken to dryness under argon and the solid dissolved in ethanol. The solution was filtered through a millipore filter directly into a sterile vial containing a physiological saline solution containing 10% Polysorbate 80, (Tween 80). The final ethanol concentration of this solution was 10%. The steroid solution (1 ml, 6–15 micro Ci) was injected via the tail vein of rats that were anesthesized with ether. The rats were sacrificed at select times after being anesthesized with ether. Blood was drained from the carcass into a beaker containing a small amount of sodium citrate solution to prohibit clotting. The organs were carefully removed, rinsed with 0.9% saline solution and blotted dry prior to weighing. The tissue distribution data were analyzed through a multifactorial analysis of variance computer program.

The distribution of radioactivity in tissues of male rats was determined at a variety of time intervals of 1 hour to 21 days following the intravenous administration of the $^{123m}$Te-labeled steroid. The major organs were removed, weighed and counted directly in a multichannel analyzer. In the first group the distribution of radioactivity was determined at 1,6 and 18 hours after administration. At the early time intervals the liver, spleen, adrenals and lungs all contained significant levels of radioactivity. The concentration of radioactivity increased rapidly in the adrenals, while the levels of radioactivity decreased or remained constant in the other organs described above. The mean percent dose/gram for the liver was 2.71 after one hour decreasing to 0.84 after 18 hours. The % dose for the spleen decreased from 2.98 after one hour to 1.29 after 18 hours. The % dose of the lungs decreased from 2.01 after one hour to 1.52 after 18 hours. The % dose for the adrenals increased from 4.51 after one hour to 22.17 after 18 hours. In the second group of animals the distribution of radioactivity was determined at one, three and seven days after injection of the labeled steroid. After one day the % dose in the liver was 1.01 decreasing to 0.23 after 7 days. The % dose in the spleen was 1.59 after one day decreasing to 0.29 after 7 days. The % dose in the lungs decreased from 2.12 after 1 day to 0.40 after 7 days. The adrenals contained 26.39% of the dose after 1 day, decreasing to 14.48% after seven days. The % dose in the thyroid was 1.23 after 1 day, decreasing to 0.74 after 3 days, remaining substantially constant to 7 days. These results are further substantiated by similar data obtained from animals in the third group which were sacrificed at seven, fourteen and twenty-one days after injection with the labeled steroid. The % dose in the liver decreased from 0.14 after 7 days to 0.03 after 21 days. The % dose in the spleen decreased from 0.32 after 7 days to 0.11 after 21 days. The % dose in the lungs decreased from 0.22 after 7 days to 0.05 after 21 days. The % dose in the thyroid remained about constant at 0.12–0.15 throughout the 7–21 day period. The % dose of adrenals decreased from 5.56% after 7 days to 1.81% after 21 days. In summary, the radioactive contents of the blood, liver and lungs are very high at early time intervals decreasing rapidly with a concomitant increase in the radioactive contents of the adrenal glands. The adrenal glands reached a maximum concentration at one to two days after injection. Female rats showed generally parallel concentrations except that the concentration of radioactivity in the ovaries was also high.

Experiments were also conducted to determine if the labeled steroid was metabolized by the adrenals and other tissues of rats. Male and female rats were injected with the $^{123m}$Te-labeled steroid of Example IV (100–300 microcuries) as described above. After three days the animals were sacrificed and the adrenals, livers, lungs and ovaries were removed. Tissues were homogenized in 45 ml of a chloroform methanol mixture (2-1, Folch medium) at 5000 rpm for 30 seconds using a Sorvall Omni-Mix device. The homogenates were filtered through cheese cloth and after addition of an equal amount of water the phases were allowed to separate. Aliquots of the lower organic phase and upper aqueous phase were counted. The aqueous phase contained very little radioactivity. The organic layers were separated and evaporated to dryness in vacuo and the resulting residues dissolved in a small volume of chloroform and applied to silicic acid columns (600–200 mesh, 2×30 cm). Fractions 25 ml in volume were collected by elution with increasing volumes of ether in benzene. Aliquots of each fraction were counted. The profiles from male rats suggested that the labeled steroid was metabolized to several products by the male adrenals. The adrenal extract from a female rat contained a non-polar radioactive component and also significant radioactivity in a region resembling the original steroid which appears to indicate a significant portion of the agent was not metabolized. The presence of non-polar radioactive components would indicate at least partial metabolism. Among the tissues which were examined the components that were observed upon chromatographic analysis of extracted lipids were consistently different and would indicate that the radioactive components represent true metabolites. The metabolism of such adrenal imaging agents is important because it indicates the compounds are stable in vivo to non-specific degradations and are metabolized in a manner similar to the natural adrenal steroid precurser cholesterol. The short residence time of the compound in the adrenal coupled with the rapid and specific accumulation of sindicates that the patient radiation dose would not be high.

The animals were anesthesized after intraperitonial injection of a sodium pentabarbitol solution (30–50 mg/kg) and scans were obtained using a rectilinear scanner equiped with a 63 hole gold collimator at a focal distance of 3 cm. The animals were scanned at 0.25 inches per minute. The camera images were obtained with an RC-type proportional counter camera utilizing a xenon gas field detector. Suitable detectors are available in the art, see for example U.S. Pat. No. 3,786,270 issued to Borkowski, et al. for Proportional Counter Radiation Camera and the publication ORNL-TM-5083 by Kopp et al. entitled "Positron Sensitive Proportional Counters Using Resistance Capacitance Position Encoding," Oak Ridge National Laboratory, 1975.

The adrenal glands of the male rats were clearly imaged one day after administration of the $^{123m}$Te-labeled steroid. Both the adrenals and ovaries of female rats were also imaged following the injection of the agent with both a rectilinear scanner and an RC-type proportional counter camera.

Additional Experiments

Tests with other steroids indicate a complex relationship between steroid structure, relative rates of entry and exit from the various body components. Steroids 3-beta-hydroxy-24-nor-23-(octyl telluro)-cholane and 3-beta-methoxy-24-(isopropyl telluro)-chol-5-ene accumulate slowly in the adrenals. The steroid prepared in Example X showed a slightly greater adrenal uptake than the steroid of Example VI. Two other steroids (3-alpha-hydroxy-24-nor-23-(isopropyl telluro)-5-beta-cholane and 3-beta-hydroxy-[(isopropyl telluro)methyl]-androst-5-ene did not concentrate in the adrenals. Based upon these observations, adrenal concentration should occur with 3-beta-hydroxy-24-nor-23-(alkyl telluro)-5-alpha-cholanes wherein the alkyl group has 1–8 carbon atoms and also with 3-beta-hydroxy-24-(alkyl telluro)chol-5-enes wherein the alkyl group has 1–8 carbon atoms.

It is seen that the general synthesis method of this invention can be adapted to the preparation of any alkyl telluro steroid merely by providing a suitable halogenated reaction site and such steroids are contemplated at equivalents of the specific steroids described herein.

According to the standard MIRD formulism, the total human radiation dose for the steroid of Example VI is 30-40 rad/millicurie; with a 200 millicurie dosage resulting in a 3-4 rad radiation dose for each adrenal. The calculated radiation dose for the steroid of Example X is slightly lower than that for the steroid of Example VI. The steroids should be administered by injection in a carrier such as Polysorbate 80, available, for example, from Fleuka, A. G. and distributed by Tridom Chemical Co., Ajuppauge, New York.

What is claimed is:

1. A process for preparing a $^{123m}$Te-labeled organic compound of the formula R-$^{123m}$Te-CH$_2$-R', R being alkyl, substituted alkyl, aryl or substituted aryl and R' being a steroidal side chain, alkyl amino acid or amino acid group, said process comprising the steps of:
    (a) reacting a $^{123m}$Te-symmetric diorgano ditelluride, R$_2$$^{123m}$Te$_2$, R being alkyl, substituted alkyl, aryl or substituted aryl, with a hydride reducing agent and a source of alkali metal ions to form an alkali metal organo telluride M-$^{123m}$Te-R;
    (b) reacting said alkali metal organo telluride with a primary halogenated organic compound R$_a$'—X, R$_a$' being a 17-alkyl steroid group having 1-4 carbon atoms in said alkyl group, an alkyl amino acid group, or a group hydrolyzable to an alkyl amino acid group.

2. The process of claim 1 wherein said symmetric diorgano ditelluride is prepared by reacting a dialkali metal ditelluride M$_2$$^{123m}$Te$_2$ with a halogenated organic compound R—X.

3. The process of claim 1 wherein said symmetric diorgano ditelluride is a diaryl ditelluride and said diaryl ditelluride is prepared by reacting an aryl magnesium halide, R-Mg-X with $^{123m}$Te.

4. The process of claim 3 wherein said diaryl ditelluride is diphenyl ditelluride.

5. The process of claim 1 wherein said symmetric diorgano ditelluride is reacted with alkali metal borohydride, MBH$_4$, to form said alkali metal organo telluride.

6. The process of claim 5 wherein said alkali metal borohydride is NaBH$_4$.

7. The process of claim 1 wherein R$_a$' is a 17-alkyl steroid group having 1-4 carbon atoms in said alkyl group.

8. The process of claim 1 wherein said primary halogenated organic compound Ra'—X is 3-beta-acetoxy-24-nor-23-bromo-5-alpha-cholane, R is isopropyl and said step (b) is performed under basic conditions to form $^{123m}$Te-3-beta-hydroxy-24-nor-23-(isopropyl telluro)-5 alpha-cholane.

9. The process of claim 1 wherein R$_a$' is an amino acid or alkyl amino acid group.

10. The process of claim 1 wherein R$_a$' is a hydantoin group or a 5-alkyl hydantoin group, and further comprising hydrolyzing the product of step (b) under basic conditions to form a $^{123m}$Te-labeled amino acid.

11. A $^{123m}$Te-labeled steroid of the formula R-$^{123m}$Te—CH$_2$—R' wherein R is an alkyl group having 1-8 carbon atoms and R' is a steroidal side chain group.

12. The $^{123m}$Te-labeled steroid of claim 11 in which R' is

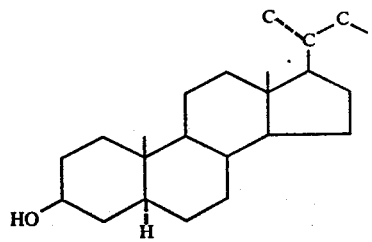

13. The $^{123m}$Te-labeled steroid of claim 12 in which R is isopropyl and having the name $^{123m}$Te-3-beta-hydroxy-24-nor-23(isopropyl telluro)-5-alpha-cholane.

14. The $^{123m}$Te-labeled steroid of claim 11 in which R' is

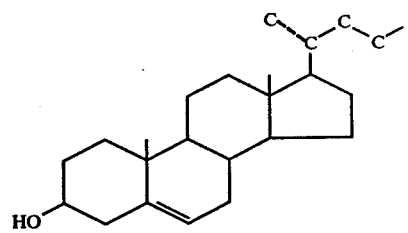

15. The $^{123m}$Te-labeled steroid of claim 14 in which R is isopropyl and having the name $^{123m}$Te-3-beta-hydroxy-24(isopropyl telluro)chol-5-ene.

16. A $^{123m}$Te-labeled amino acid of the formula

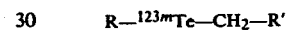

wherein R is an alkyl, aryl, substituted alkyl or substituted aryl and R' is an amino acid or alkyl amino acid group.

17. The $^{123m}$Te-labeled amino acid of claim 16 wherein R is phenyl or methyl and R' is CH$_2$CR"(NH$_2$)COOH, R" being hydrogen, or alkyl.

18. The $^{123m}$Te-labeled amino acid of claim 17 wherein R" is methyl or ethyl and having the name DL-alpha-amino-alpha-methyl-beta(phenyl telluro)-proprionic acid or DL-alpha-amino-alpha-ethyl-beta(-phenyl telluro)proprionic acid.

19. The process of claim 1 wherein Ra' is an alpha amino acid group.

20. The process of claim 10 wherein Ra' is a hydantoin group.

21. The process of claim 9 wherein said symmetric diorgano ditelluride is a diaryl ditelluride prepared by reacting an aryl magnesium halide R—Mg—X with $^{123m}$Te.

22. The process of claim 21 wherein said diaryl ditelluride is diphenyl ditelluride.

23. The $^{123m}$Te-labeled steroid of claim 11 in which said steroidal side chain has 1-4 carbon atoms.

24. The $^{123m}$Te-labeled steroid of claim 11 having the name 3-hydroxy-24-nor-23-(isopentyl telluro)-5-cho-lane.

25. The $^{123m}$Te-labeled steroid of claim 11 having the name 3-beta-hydroxy-24-nor-23-(isopentyl telluro)-5-alpha-cholane.

26. The $^{123m}$Te-labeled steroid of claim 11 having the name 3-beta-hydroxy-24-nor-23-(octyl telluro)-cholane.

27. The $^{123m}$Te-labeled steroid of claim 11 having the name 3-beta-methoxy-24-(isopropyl telluro)-chol-5-ene.

28. The $^{123m}$Te-labeled amino acid of claim 16 in which R' is an alpha amino acid.

29. The $^{123m}$Te-labeled amino acid of claim 28 having the name DL-alpha-amino-gamma-(phenyl telluro)-butyric acid.

30. The $^{123m}$Te-labeled amino acid of claim 28 having the name DL-alpha-amino-gamma-(methyl telluro)-butyric acid.

31. The process of claim 1 wherein Ra' is a 17-alkyl steroid group wherein the 3-beta position is substituted with hydroxy, methoxy or esters of palmitic, steric, or oleic acid.

* * * * *